United States Patent [19]

Stüber et al.

[11] Patent Number: 6,143,493
[45] Date of Patent: Nov. 7, 2000

[54] HCMV-SPECIFIC PEPTIDES, AGENTS THEREFOR AND THE USE THEREOF

[75] Inventors: Werner Stüber, Lahntal; Leszek Wieczorek; Robert Ziegelmaier, both of Marburg, all of Germany

[73] Assignee: Dade Behring Marburg GmbH, Marburg, Germany

[21] Appl. No.: 08/462,211

[22] Filed: Jun. 5, 1995

Related U.S. Application Data

[62] Division of application No. 08/388,883, Feb. 13, 1995, Pat. No. 5,859,185, which is a continuation of application No. 08/200,305, Feb. 23, 1994, abandoned, which is a continuation of application No. 07/936,219, Aug. 27, 1992, abandoned.

[30] Foreign Application Priority Data

Aug. 29, 1991 [DE] Germany ............................. 41 28 684

[51] Int. Cl.⁷ .......................... C12Q 1/70; G01N 33/569; G01N 33/543; C07K 4/02
[52] U.S. Cl. .............................. 435/5; 435/973; 435/975; 530/324; 530/325; 530/326; 530/327; 530/328; 530/329; 530/403
[58] Field of Search ............................... 435/5, 7.1, 7.92, 435/975, 973; 530/324, 325, 326, 327, 329, 328, 330, 350, 333, 403

[56] References Cited

FOREIGN PATENT DOCUMENTS

| 0 252 531 A1 | 1/1988 | European Pat. Off. . |
| 0 268 014 A2 | 5/1988 | European Pat. Off. . |
| 0 271 201 A2 | 6/1988 | European Pat. Off. . |
| 36 19902 | 3/1988 | Germany ....................... C12N 15/00 |
| WO 89/01628 | 2/1989 | WIPO . |

OTHER PUBLICATIONS

Breipohl et al., "Synthesis and Application of Acid Labile Anchor Groups for the Synthesis of Peptide Amides by Fmoc–solid–phase Peptide Synthesis," Int. J. Peptide Protein Res. 34:262–67 (1989).

Novák et al., "Mapping of Serologically Relevant Regions of Human Cytomegalovirus Phosphoprotein pp150 Using Synthetic Peptides," Journal ofGeneral Virology 72:1409–13 (1991).

Jahn et al., "Map Position and Nucleotide Sequence of the Gene for the Large Structural Phosphoprotein of Human Cytomegalovirus," Journal of Virology 61 (5) :1358–67 (1987).

Schaffhausen, B.S., "Designing and Using Site–Specific Antibodies to Synthetic Peptides,"Hybridoma Technology in the Biosciences and Medicine, pp. 355–67 (Springer, ed., 1985).

Nakane et al., "Peroxidase–Labeled Antibody, A New Method of Conjugation," J. of Histochem. and Cytochem. 22(12):1084–91 (1974).

Ishikawa et al., "Enzyme–Labeling of Antibodies and Their Fragments for Enzyme Immunoassay and Immunohistochemical Staining," Journal of Immunoassay 4(30:209–327 (1983).

*Primary Examiner*—Mary E. Mosher
*Attorney, Agent, or Firm*—Finnegan, Henderson, Farabow, Garrett and Dunner, L.L.P.

[57] ABSTRACT

The invention relates to peptides for the immunochemical determination of human cytomegalovirus (HCMV)-specific antibodies and HCMV antigens, and to agents suitable for this method and to the use thereof.

58 Claims, No Drawings

SEQUENCE LISTING (1) GENERAL INFORMATION:

(iii) NUMBER OF SEQUENCES: 49

(2) INFORMATION FOR SEQ ID NO:1:

(i) SEQUENCE CHARACTERISTICS:
      (A) LENGTH: 7 amino acids
      (B) TYPE: amino acid
      (D) TOPOLOGY: linear (ii) MOLECULE TYPE: peptide (xi) SEQUENCE DESCRIPTION: SEQ ID NO:1:

Gly Ala Gly Ala Ala Ile Leu
1           5

(2) INFORMATION FOR SEQ ID NO:2:

(i) SEQUENCE CHARACTERISTICS:
      (A) LENGTH: 5 amino acids
      (B) TYPE: amino acid
      (D) TOPOLOGY: linear (ii) MOLECULE TYPE: peptide (xi) SEQUENCE DESCRIPTION: SEQ ID NO:2:

Arg Ala Trp Ala Leu
1           5

(2) INFORMATION FOR SEQ ID NO:3:

(i) SEQUENCE CHARACTERISTICS:
      (A) LENGTH: 6 amino acids
      (B) TYPE: amino acid
      (D) TOPOLOGY: linear (ii) MOLECULE TYPE: peptide (xi) SEQUENCE DESCRIPTION: SEQ ID NO:3:

Ala Ser Arg Asp Ala Ala
1           5

(2) INFORMATION FOR SEQ ID NO:4:

(i) SEQUENCE CHARACTERISTICS:
        (A) LENGTH: 26 amino acids
        (B) TYPE: amino acid
        (D) TOPOLOGY: linear (ii) MOLECULE TYPE: peptide (xi) SEQUENCE DESCRIPTION: SEQ ID NO:4:

Ala Tyr Lys Phe Glu Gln Pro Thr Leu Thr Phe Gly Ala Gly Val Asn
1               5                  10                  15

Val Pro Ala Gly Ala Gly Ala Ala Ile Leu
            20                  25

(2) INFORMATION FOR SEQ ID NO:5:

(i) SEQUENCE CHARACTERISTICS:
        (A) LENGTH: 28 amino acids
        (B) TYPE: amino acid
        (D) TOPOLOGY: linear (ii) MOLECULE TYPE: peptide (xi) SEQUENCE DESCRIPTION: SEQ ID NO:5:

Phe Glu Gln Pro Thr Leu Thr Phe Gly Ala Gly Val Asn Val Pro Ala
1               5                  10                  15

Gly Ala Gly Ala Ala Ile Leu Thr Pro Thr Pro Val
            20                  25

(2) INFORMATION FOR SEQ ID NO:6:

(i) SEQUENCE CHARACTERISTICS:
        (A) LENGTH: 33 amino acids
        (B) TYPE: amino acid
        (D) TOPOLOGY: linear (ii) MOLECULE TYPE: peptide (xi) SEQUENCE DESCRIPTION: SEQ ID NO:6:

Phe Glu Gln Pro Thr Leu Thr Phe Gly Ala Gly Val Asn Val Pro Ala
1               5                  10                  15

Gly Ala Gly Ala Ala Ile Leu Thr Pro Thr Pro Val Asn Pro Ser Thr
            20                  25                  30

Ala (2) INFORMATION FOR SEQ ID NO:7:

(i) SEQUENCE CHARACTERISTICS:
        (A) LENGTH: 37 amino acids
        (B) TYPE: amino acid
        (D) TOPOLOGY: linear (ii) MOLECULE TYPE: peptide (xi) SEQUENCE DESCRIPTION: SEQ ID NO:7:

Phe Glu Gln Pro Thr Leu Thr Phe Gly Ala Gly Val Asn Val Pro
1               5                  10                  15

Ala Gly Ala Gly Ala Ala Ile Leu Thr Pro Thr Pro Val Asn Pro Ser
            20                  25                  30

Thr Ala Pro Ala Pro Ala
            35

(2) INFORMATION FOR SEQ ID NO:8:

(i) SEQUENCE CHARACTERISTICS:
        (A) LENGTH: 34 amino acids (B) TYPE: amino acid
            (D) TOPOLOGY: linear (ii) MOLECULE TYPE: peptide (xi) SEQUENCE DESCRIPTION: SEQ ID NO:8:

Pro Thr Leu Thr Phe Gly Ala Gly Val Asn Val Pro Ala Gly Ala Gly
1               5                   10                  15

Ala Ala Ile Leu Thr Pro Thr Pro Val Asn Pro Ser Thr Ala Pro Ala
            20                  25                  30

Pro Ala (2) INFORMATION FOR SEQ ID NO:9:

(i) SEQUENCE CHARACTERISTICS:
        (A) LENGTH: 35 amino acids
        (B) TYPE: amino acid
        (D) TOPOLOGY: linear (ii) MOLECULE TYPE: peptide (xi) SEQUENCE DESCRIPTION: SEQ ID NO:9:

Pro Thr Leu Thr Phe Gly Ala Gly Val Asn Val Pro Ala Gly Ala Gly
1               5                   10                  15

Ala Ala Ile Leu Thr Pro Thr Pro Val Asn Pro Ser Thr Ala Pro Ala
            20                  25                  30

Pro Ala Pro
        35

(2) INFORMATION FOR SEQ ID NO:10:

(i) SEQUENCE CHARACTERISTICS:
        (A) LENGTH: 19 amino acids
        (B) TYPE: amino acid
        (D) TOPOLOGY: linear (ii) MOLECULE TYPE: peptide (xi) SEQUENCE DESCRIPTION: SEQ ID NO:10:

Val Asn Val Pro Ala Gly Ala Gly Ala Ala Ile Leu Thr Pro Thr Pro
1               5                   10                  15

Val Asn Pro (2) INFORMATION FOR SEQ ID NO:11:

(i) SEQUENCE CHARACTERISTICS:
        (A) LENGTH: 21 amino acids
        (B) TYPE: amino acid
        (D) TOPOLOGY: linear (ii) MOLECULE TYPE: peptide (xi) SEQUENCE DESCRIPTION: SEQ ID NO:11:

Pro Ala Gly Ala Gly Ala Ala Ile Leu Thr Pro Thr Pro Val Asn Pro
1               5                   10                  15

Ser Thr Ala Pro Ala
            20

(2) INFORMATION FOR SEQ ID NO:12:

(i) SEQUENCE CHARACTERISTICS:
        (A) LENGTH: 31 amino acids
        (B) TYPE: amino acid
        (D) TOPOLOGY: linear (ii) MOLECULE TYPE: peptide (xi) SEQUENCE DESCRIPTION: SEQ ID NO:12:

Val Asn Val Pro Ala Gly Ala Gly Ala Ala Ile Leu Thr Pro Thr Pro
1               5                   10                  15

Val Asn Pro Ser Thr Ala Pro Ala Pro Ala Pro Thr Pro Thr Phe
            20                  25                  30

(2) INFORMATION FOR SEQ ID NO:13:

(i) SEQUENCE CHARACTERISTICS:
        (A) LENGTH: 31 amino acids
        (B) TYPE: amino acid
        (D) TOPOLOGY: linear (ii) MOLECULE TYPE: peptide (xi) SEQUENCE DESCRIPTION: SEQ ID NO:13:

Pro Ala Gly Ala Gly Ala Ala Ile Leu Thr Pro Thr Pro Val Asn Pro
1               5                   10                  15

Ser Thr Ala Pro Ala Pro Ala Pro Thr Pro Thr Phe Ala Gly Thr
            20                  25                  30

(2) INFORMATION FOR SEQ ID NO:14:

(i) SEQUENCE CHARACTERISTICS:
        (A) LENGTH: 30 amino acids
        (B) TYPE: amino acid
        (D) TOPOLOGY: linear (ii) MOLECULE TYPE: peptide (xi) SEQUENCE DESCRIPTION: SEQ ID NO:14:

Gly Ala Gly Val Asn Val Pro Ala Gly Ala Gly Ala Ala Ile Leu Thr
1               5                   10                  15

Pro Thr Pro Val Asn Pro Ser Thr Ala Pro Ala Pro Ala Pro
            20                  25                  30

(2) INFORMATION FOR SEQ ID NO:15:

(i) SEQUENCE CHARACTERISTICS:
        (A) LENGTH: 32 amino acids
        (B) TYPE: amino acid
        (D) TOPOLOGY: linear (ii) MOLECULE TYPE: peptide (xi) SEQUENCE DESCRIPTION: SEQ ID NO:15:

Gly Ala Gly Ala Ala Ile Leu Thr Pro Thr Pro Val Asn Pro Ser Thr
1               5                   10                  15

Ala Pro Ala Pro Ala Pro Thr Pro Thr Phe Ala Gly Thr Gln Thr Pro
            20                  25                  30

(2) INFORMATION FOR SEQ ID NO:16:

(i) SEQUENCE CHARACTERISTICS:
        (A) LENGTH: 41 amino acids
        (B) TYPE: amino acid
        (D) TOPOLOGY: linear (ii) MOLECULE TYPE: peptide (xi) SEQUENCE DESCRIPTION: SEQ ID NO:16:

Ala Tyr Lys Phe Gly Gln Pro Thr Leu Thr Phe Gly Ala Gly Val Asn
1               5                   10                  15

-continued

```
Val Pro Ala Gly Ala Gly Ala Ala Ile Leu Thr Pro Thr Pro Val Asn
            20                  25                  30

Pro Ser Thr Ala Pro Ala Pro Ala Pro
        35                  40

(2) INFORMATION FOR SEQ ID NO:17:

(i) SEQUENCE CHARACTERISTICS:
        (A) LENGTH: 51 amino acids
        (B) TYPE: amino acid
        (D) TOPOLOGY: linear (ii) MOLECULE TYPE: peptide (xi) SEQUENCE DESCRIPTION: SEQ ID NO:17:

Ala Tyr Lys Phe Glu Gln Pro Thr Leu Thr Phe Gly Ala Gly Val Asn
1               5                  10                  15

Val Pro Ala Gly Ala Gly Ala Ala Ile Leu Thr Pro Thr Pro Val Asn
            20                  25                  30

Pro Ser Thr Ala Pro Ala Pro Ala Pro Thr Pro Thr Phe Ala Gly Thr
        35                  40                  45

Gln Thr Pro
    50

(2) INFORMATION FOR SEQ ID NO:18:

(i) SEQUENCE CHARACTERISTICS:
        (A) LENGTH: 41 amino acids
        (B) TYPE: amino acid
        (D) TOPOLOGY: linear (ii) MOLECULE TYPE: peptide (xi) SEQUENCE DESCRIPTION: SEQ ID NO:18:

Ala Tyr Lys Phe Glu Gln Pro Thr Leu Thr Phe Gly Ala Gly Val Asn
1               5                  10                  15

Val Pro Ala Gly Ala Gly Ala Ala Ile Leu Thr Pro Thr Pro Val Asn
            20                  25                  30

Pro Ser Thr Ala Pro Ala Pro Ala Pro
        35                  40

(2) INFORMATION FOR SEQ ID NO:19:

(i) SEQUENCE CHARACTERISTICS:
        (A) LENGTH: 29 amino acids
        (B) TYPE: amino acid
        (D) TOPOLOGY: linear (ii) MOLECULE TYPE: peptide (xi) SEQUENCE DESCRIPTION: SEQ ID NO:19:

Gly Ala Gly Val Asn Val Pro Ala Gly Ala Gly Ala Ala Ile Leu Thr
1               5                  10                  15

Pro Thr Pro Val Asn Pro Ser Thr Ala Pro Ala Pro Ala
            20                  25

(2) INFORMATION FOR SEQ ID NO:20:

(i) SEQUENCE CHARACTERISTICS:
        (A) LENGTH: 25 amino acids
        (B) TYPE: amino acid
        (D) TOPOLOGY: linear (ii) MOLECULE TYPE: peptide
```

(xi) SEQUENCE DESCRIPTION: SEQ ID NO:20:

Asp Met Asn Pro Ala Asn Trp Pro Arg Glu Arg Ala Trp Ala Leu Lys
1               5                   10                  15

Asn Pro His Leu Ala Tyr Asn Pro Phe
            20                  25

(2) INFORMATION FOR SEQ ID NO:21:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO:21:

Asp Met Asn Pro Ala Asn Trp Pro Arg Glu Arg Ala Trp Ala Leu Lys
1               5                   10                  15

Asn Pro His Leu
            20

(2) INFORMATION FOR SEQ ID NO:22:

(i) SEQUENCE CHARACTERISTICS:
        (A) LENGTH: 17 amino acids
        (B) TYPE: amino acid
        (D) TOPOLOGY: linear (ii) MOLECULE TYPE: peptide (xi) SEQUENCE DESCRIPTION: SEQ ID NO:22:

Pro Ala Asn Trp Pro Arg Glu Arg Ala Trp Ala Leu Lys Asn Pro His
1               5                   10                  15

Leu (2) INFORMATION FOR SEQ ID NO:23:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO:23:

Pro Ala Asn Trp Pro Arg Glu Arg Ala Trp Ala Leu Lys Asn Pro His
1               5                   10                  15

Leu Ala Tyr Asn
            20

(2) INFORMATION FOR SEQ ID NO:24:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO:24:

Trp Pro Arg Glu Arg Ala Trp Ala Leu Lys Asn Pro His Leu Ala Tyr
1               5                   10                  15

Asn Pro Phe Arg
            20

(2) INFORMATION FOR SEQ ID NO:25:

(i) SEQUENCE CHARACTERISTICS:
        (A) LENGTH: 21 amino acids
        (B) TYPE: amino acid
        (D) TOPOLOGY: linear (ii) MOLECULE TYPE: peptide (xi) SEQUENCE DESCRIPTION: SEQ ID NO:25:

```
Glu Arg Ala Trp Ala Leu Lys Asn Pro His Leu Ala Tyr Asn Pro Phe
1               5                   10                  15

Arg Met Pro Thr Thr
            20
```

(2) INFORMATION FOR SEQ ID NO:26:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (xi) SEQUENCE DESCRIPTION: SEQ ID NO:26:

```
Asp Met Asn Pro Ala Asn Trp Pro Arg Glu Arg Ala Trp Ala Leu
1               5                   10                  15
```

(2) INFORMATION FOR SEQ ID NO:27:

(i) SEQUENCE CHARACTERISTICS:
        (A) LENGTH: 17 amino acids
        (B) TYPE: amino acid
        (D) TOPOLOGY: linear (ii) MOLECULE TYPE: peptide (xi) SEQUENCE DESCRIPTION: SEQ ID NO:27:

```
Ala Asn Trp Pro Arg Glu Arg Ala Trp Ala Leu Lys Asn Pro His Leu
1               5                   10                  15

Ala
```

(2) INFORMATION FOR SEQ ID NO:28:

(i) SEQUENCE CHARACTERISTICS:
        (A) LENGTH: 33 amino acids
        (B) TYPE: amino acid
        (D) TOPOLOGY: linear (ii) MOLECULE TYPE: peptide (xi) SEQUENCE DESCRIPTION: SEQ ID NO:28:

```
Asp Met Asn Pro Ala Asn Trp Pro Arg Glu Arg Ala Trp Ala Leu Lys
1               5                   10                  15

Asn Pro His Leu Ala Tyr Asn Pro Phe Arg Met Pro Thr Thr Ser Thr
            20                  25                  30

Ala
```

(2) INFORMATION FOR SEQ ID NO:29:

(i) SEQUENCE CHARACTERISTICS:
        (A) LENGTH: 15 amino acids
        (B) TYPE: amino acid
        (D) TOPOLOGY: linear (ii) MOLECULE TYPE: peptide

```
        (xi) SEQUENCE DESCRIPTION: SEQ ID NO:29:

Arg Ala Trp Ala Leu Lys Asn Pro His Leu Ala Tyr Asn Pro Phe
1               5                   10                  15

(2) INFORMATION FOR SEQ ID NO:30:

(i) SEQUENCE CHARACTERISTICS:
            (A) LENGTH: 14 amino acids
            (B) TYPE: amino acid
            (D) TOPOLOGY: linear (ii) MOLECULE TYPE: peptide (xi) SEQUENCE DESCRIPTION: SEQ ID NO:30:

Pro Arg Ala Ala Val Thr Gln Thr Ala Ser Arg Asp Ala Ala
1               5                   10

(2) INFORMATION FOR SEQ ID NO:31:

(i) SEQUENCE CHARACTERISTICS:
            (A) LENGTH: 17 amino acids
            (B) TYPE: amino acid
            (D) TOPOLOGY: linear (ii) MOLECULE TYPE: peptide (xi) SEQUENCE DESCRIPTION: SEQ ID NO:31:

Ala Ser Arg Asp Ala Ala Asp Glu Val Trp Ala Leu Arg Asp Gln Thr
1               5                   10                  15

Ala (2) INFORMATION FOR SEQ ID NO:32:

(i) SEQUENCE CHARACTERISTICS:
            (A) LENGTH: 5 amino acids
            (B) TYPE: amino acid
            (D) TOPOLOGY: linear (ii) MOLECULE TYPE: peptide (xi) SEQUENCE DESCRIPTION: SEQ ID NO:32:

Phe Ala Phe Ala Phe
1               5

(2) INFORMATION FOR SEQ ID NO:33:

(i) SEQUENCE CHARACTERISTICS:
            (A) LENGTH: 162 amino acids
            (B) TYPE: amino acid
            (D) TOPOLOGY: linear (ii) MOLECULE TYPE: peptide (xi) SEQUENCE DESCRIPTION: SEQ ID NO:33:

Asp Pro Arg Phe Thr Asp Thr Leu Val Asp Ile Thr Asp Thr Glu Thr
1               5                   10                  15

Ser Ala Lys Pro Pro Val Thr Thr Ala Tyr Lys Phe Glu Gln Pro Thr
                20                  25                  30

Leu Thr Phe Gly Ala Gly Val Asn Val Pro Ala Gly Ala Gly Ala Ala
            35                  40                  45

Ile Leu Thr Pro Thr Pro Val Asn Pro Ser Thr Ala Pro Ala Pro Ala
        50                  55                  60

Pro Thr Pro Thr Phe Ala Gly Thr Gln Thr Pro Val Asn Gly Asn Ser
65                  70                  75                  80
```

```
Pro Trp Ala Pro Thr Ala Pro Leu Pro Gly Asp Met Asn Pro Ala Asn
                85                  90                  95

Trp Pro Arg Glu Arg Ala Trp Ala Leu Lys Asn Pro His Leu Ala Tyr
            100                 105                 110

Asn Pro Phe Arg Met Pro Thr Thr Ser Thr Ala Ser Gln Asn Thr Val
        115                 120                 125

Ser Thr Thr Pro Arg Arg Pro Ser Thr Pro Arg Ala Ala Val Thr Gln
    130                 135                 140

Thr Ala Ser Arg Asp Ala Ala Asp Glu Val Trp Ala Leu Arg Asp Gln
145                 150                 155                 160

Thr Ala (2) INFORMATION FOR SEQ ID NO:34:

(i) SEQUENCE CHARACTERISTICS:
        (A) LENGTH: 22 amino acids
        (B) TYPE: amino acid
        (D) TOPOLOGY: linear (ii) MOLECULE TYPE: peptide (xi) SEQUENCE DESCRIPTION: SEQ ID NO:34:

Asp Pro Arg Phe Thr Asp Thr Leu Val Asp Ile Thr Asp Thr Glu Thr
1               5                   10                  15

Ser Ala Lys Pro Pro Val
            20

(2) INFORMATION FOR SEQ ID NO:35:

(i) SEQUENCE CHARACTERISTICS:
        (A) LENGTH: 21 amino acids
        (B) TYPE: amino acid
        (D) TOPOLOGY: linear (ii) MOLECULE TYPE: peptide (xi) SEQUENCE DESCRIPTION: SEQ ID NO:35:

Ala Pro Ala Pro Ala Pro Thr Pro Thr Phe Ala Gly Thr Gln Thr Pro
1               5                   10                  15

Val Asn Gly Asn Ser
            20

(2) INFORMATION FOR SEQ ID NO:36:

(i) SEQUENCE CHARACTERISTICS:
        (A) LENGTH: 13 amino acids
        (B) TYPE: amino acid
        (D) TOPOLOGY: linear (ii) MOLECULE TYPE: peptide (xi) SEQUENCE DESCRIPTION: SEQ ID NO:36:

Ala Pro Thr Ala Pro Leu Pro Gly Asp Met Asn Pro Ala
1               5                   10

(2) INFORMATION FOR SEQ ID NO:37:

(i) SEQUENCE CHARACTERISTICS:
        (A) LENGTH: 22 amino acids
        (B) TYPE: amino acid
        (D) TOPOLOGY: linear (ii) MOLECULE TYPE: peptide
```

(xi) SEQUENCE DESCRIPTION: SEQ ID NO:37:

Gln Asn Thr Val Ser Thr Thr Pro Arg Arg Pro Ser Thr Pro Arg Ala
1               5                   10                  15

Ala Val Thr Gln Thr Ala
            20

(2) INFORMATION FOR SEQ ID NO:38:

(i) SEQUENCE CHARACTERISTICS:
        (A) LENGTH: 16 amino acids
        (B) TYPE: amino acid
        (D) TOPOLOGY: linear (ii) MOLECULE TYPE: peptide (xi) SEQUENCE DESCRIPTION: SEQ ID NO:38:

Gly Thr Gln Thr Pro Val Asn Gly Asn Ser Pro Trp Ala Pro Thr Ala
1               5                   10                  15

(2) INFORMATION FOR SEQ ID NO:39:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (xi) SEQUENCE DESCRIPTION: SEQ ID NO:39:

Pro Val Thr Thr Ala Tyr Lys Phe Glu Gln Pro Thr Leu Thr Phe
1               5                   10                  15

(2) INFORMATION FOR SEQ ID NO:40:

(i) SEQUENCE CHARACTERISTICS:
        (A) LENGTH: 18 amino acids
        (B) TYPE: amino acid
        (D) TOPOLOGY: linear (ii) MOLECULE TYPE: peptide (xi) SEQUENCE DESCRIPTION: SEQ ID NO:40:

Leu Thr Phe Gly Ala Gly Val Asn Val Pro Ala Gly Ala Gly Ala Ala
1               5                   10                  15

Ile Leu (2) INFORMATION FOR SEQ ID NO:41:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (xi) SEQUENCE DESCRIPTION: SEQ ID NO:41:

Ile Leu Thr Pro Thr Pro Val Asn Pro Ser Thr Ala Pro Ala
1               5                   10

(2) INFORMATION FOR SEQ ID NO:42:

(i) SEQUENCE CHARACTERISTICS:
        (A) LENGTH: 15 amino acids
        (B) TYPE: amino acid
        (D) TOPOLOGY: linear (ii) MOLECULE TYPE: peptide -continued (xi) SEQUENCE DESCRIPTION: SEQ ID NO:42:

Pro Phe Arg Met Pro Thr Thr Ser Thr Ala Ser Gln Asn Thr Val
1               5                  10                  15

(2) INFORMATION FOR SEQ ID NO:43:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (xi) SEQUENCE DESCRIPTION: SEQ ID NO:43:

Glu Thr Ser Ala Lys Pro Pro Val Thr Thr Ala Tyr Lys Phe Glu
1               5                  10                  15

(2) INFORMATION FOR SEQ ID NO:44:

(i) SEQUENCE CHARACTERISTICS:
        (A) LENGTH: 13 amino acids
        (B) TYPE: amino acid
        (D) TOPOLOGY: linear (ii) MOLECULE TYPE: peptide (xi) SEQUENCE DESCRIPTION: SEQ ID NO:44:

Lys Phe Glu Gln Pro Thr Leu Thr Phe Gly Ala Gly Val
1               5                  10

(2) INFORMATION FOR SEQ ID NO:45:

(i) SEQUENCE CHARACTERISTICS:
        (A) LENGTH: 11 amino acids
        (B) TYPE: amino acid
        (D) TOPOLOGY: linear (ii) MOLECULE TYPE: peptide (xi) SEQUENCE DESCRIPTION: SEQ ID NO:45:

Ala Gly Ala Ala Ile Leu Thr Pro Thr Pro Val
1               5                  10

(2) INFORMATION FOR SEQ ID NO:46:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (xi) SEQUENCE DESCRIPTION: SEQ ID NO:46:

Val Asn Pro Ser Thr Ala Pro Ala Pro Ala Pro Thr
1               5                  10

(2) INFORMATION FOR SEQ ID NO:47:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (xi) SEQUENCE DESCRIPTION: SEQ ID NO:47:

His Leu Ala Tyr Asn Pro Phe Arg Met Pro Thr Thr Ser Thr Ala

-continued

```
1               5              10            15
```

(2) INFORMATION FOR SEQ ID NO:48:

(i) SEQUENCE CHARACTERISTICS:
        (A) LENGTH: 11 amino acids
        (B) TYPE: amino acid
        (D) TOPOLOGY: linear (ii) MOLECULE TYPE: peptide (xi) SEQUENCE DESCRIPTION: SEQ ID NO:48:

```
Asp Pro Arg Phe Thr Asp Thr Leu Val Asp Ile
1               5                   10
```

(2) INFORMATION FOR SEQ ID NO:49:

(i) SEQUENCE CHARACTERISTICS:
        (A) LENGTH: 23 amino acids
        (B) TYPE: amino acid
        (D) TOPOLOGY: linear (ii) MOLECULE TYPE: peptide (xi) SEQUENCE DESCRIPTION: SEQ ID NO:49:

```
Ile Thr Asp Thr Glu Thr Ser Ala Lys Pro Pro Val Thr Thr Ala Tyr
1               5                   10                  15

Lys Phe Glu Gln Pro Thr Leu
            20
```

HCMV-SPECIFIC PEPTIDES, AGENTS THEREFOR AND THE USE THEREOF

This a division of application Ser. No. 08/388,883, filed Feb. 13, 1995, U.S. Pat. No. 5,859,185 which is a continuation of application Ser. No. 08/200,305, filed Feb. 23, 1994, abandoned, which is is a continuation of application Ser. No. 07/936,219, filed Aug. 27, 1992, abandoned.

The invention relates to peptides for the immunochemical determination of human cytomegalovirus (HCMV)-specific antibodies and HCMV antigens, and to agents suitable for this method and to the use thereof.

Used to date in diagnosis to check the HCMV immunity status has been, for example, an enzyme immunoassay. This assay detected antibodies specifically directed against HCMV. The antigen employed was virus material which was generally grown on human fibroblasts in an elaborate cell culture and, after processing, attached to a surface utilizable in diagnosis, for example an ELISA microtiter plate.

Obtaining HCMV antigen for antibody detection from cell culture is generally very time-consuming and costly and is associated with a possible risk of infection for the people engaged therein. To use this antigen in an immunological diagnostic assay, the virus must be obtained from the cell culture medium or even from the cells themselves or at least be presented in a form which makes an immunological reaction possible. Since further purification of this material by biochemical methods is very elaborate and involves large losses, for example cell-bound virus material is only liberated by ultrasonification and is employed directly after dilution for coating microtiter plates, for example. In this case it is not only virus-specific structures which are bound to the surfaces of the microtiter plate wells but also to a greater extent cell-specific proteins. The latter in turn may with certain diseases, for example autoimmune diseases, easily lead to false-positive results and accordingly to misdiagnosis. To determine the number of false-positive signals, generally investigation material from non-infected cell cultures is therefore used as control. This inevitably doubles the complexity of the assay and the costs per sample.

A distinct improvement in the described method is represented by the use of recombinant proteins which can be prepared in high yield in a heterologous system, for example in *Escherichia coli*. Possible HCMV infection is generally ruled out by cloning and expression of defined regions of the virus. In addition there is a possibility of a differential diagnosis directed at specific virus proteins. However, to employ recombinant proteins in immunological assays it must be ensured that no contaminating constituents of the host cell lead to false-positive reactions with serum samples. Specific, usually very elaborate purification methods are needed in this case to achieve this quality.

Furthermore, the recombinant proteins must carry immunologically reactive epitopes which unambiguously define the immune status and have a diagnostic relevance or a relevance for the production of a protective status (vaccine). In most cases these epitopes cannot be prepared in native form by recombinant techniques because they represent foreign proteins for most of the expression systems used and rapidly undergo proteolytic degradation. For this reason they are usually expressed as hybrid proteins, with a host-protein for example β-galactosidase in the case of *Escherichia coli*, as fusion partner stabilizing the expression product. However, this foreign portion of the fusion may, owing to the following purification steps, give rise to false-positive reactions which impede the diagnostic use of recombinant proteins.

A protein has now been identified which is generally suitable for determining the immune status for HCMV. For this protein, the protein pp150, both the complete DNA sequence as well as a section 162 amino acids long (the XhoI-PstI restriction fragment, called pXP1 cloned as plasmid) are known which contains sequences relevant for unambiguous diagnosis (Jahn, G. et al. (1987), J. Virol. 61, 1358–1367).

J. Novak et al. (J. Novak et al. (1991), J. Gen. Virol. 72, 1409–1413) have now found, with the aid of synthetically prepared peptides, on the complete pp150 protein only three immunoreactive regions, of which two regions are located between the cleavage sites of the restriction endonucleases XhoI and PstI (XP1 region, Tab. 1).

The amino acids are reproduced in Tab. 1 as single letter code according to the following key: Ala=A, Arg=R, Asn=N, Asp=D, Cys=C, Gln=Q, Glu=E, Gly=G, His=H, Ile=I, Leu=L, Lys=K, Met=M, Phe=F, Pro=P, Ser=S, Thr=T, Trp=W, Tyr=Y and Val=V.

The object on which the present invention was based was first to develop an assay with which it is possible to detect HCMV infections as early as possible and with high specificity.

Surprisingly, it has now been found, that it was not possible to confirm the immunoreactive regions found by Novak et al. on the XP1 region but, instead of this, three immunoreactive regions different from Novak et al. were found. It was additionally found that virtually complete determination of the immune status is possible in particular by using all three epitopes according to the invention in an immunoassay.

The invention therefore relates to peptides which react specifically with antibodies against HCMV, and which contain at least one of the following amino-acid sequences:

Peptide 1: gly ala gly ala ala ile leu (SEQ ID NO:1),

Peptide 2: arg ala trp ala leu (SEQ ID NO:2), and/or

Peptide 3: ala ser arg asp ala ala (SEQ ID NO:3).

Peptide 1 further contains 0–22 additional N-terminal amino acids and 0–25 C-terminal amino acids. Peptide 2 further contains 0–18 additional N-terminal amino acids and 0–18 additional C-terminal amino acids. Peptide 3 further contains 0–11 additional N-terminal amino acids and 0–11 C-terminal amino acids. The additional amino acids may be any appropriate amino acids.

Preferred peptides are for peptide 1:

```
1.1
ala tyr lys phe glu gln pro thr leu thr phe gly ala gly   (SEQ ID NO:4)
val asn val pro ala gly ala gly ala ala ile leu 1.2
phe glu gln pro thr leu thr phe gly ala gly val asn val   (SEQ ID NO:5)
pro ala gly ala gly ala ala ile leu thr pro thr pro val
```

-continued 1.3
phe glu gln pro thr leu thr phe gly ala gly val asn val   (SEQ ID NO:6)
pro ala gly ala gly ala ala ile leu thr pro thr pro val
asn pro ser thr ala 1.4
phe glu gln pro thr thr leu thr phe gly ala gly val asn   (SEQ ID NO:7)
val pro ala gly ala gly ala ala iel leu thr pro thr pro
val asn pro ser thr ala pro ala pro ala 1.5
pro thr leu thr phe gly ala gly val asn val pro ala gly   (SEQ ID NO:8)
ala gly ala ala ile leu thr pro thr pro val asn pro ser
thr ala pro ala pro ala 1.6
pro thr leu thr phe gly ala gly val asn val pro ala gly   (SEQ ID NO:9)
ala gly ala ala ile leu thr pro thr pro val asn pro ser
thr ala pro ala pro ala pro NH$_2$ 1.7
val asn val pro ala gly ala gly ala ala ile leu thr pro   (SEQ ID NO:10)
thr pro val asn pro 1.8
pro ala gly ala gly ala ala ile leu thr pro thr pro val   (SEQ ID NO:11)
asn pro ser thr ala pro ala 1.9
val asn val pro ala gly ala gly ala ala ile leu thr pro   (SEQ ID NO:12)
thr pro val asn pro ser thr ala pro ala pro ala pro thr
pro thr phe 1.10
pro ala gly ala gly ala ala ile leu thr pro thr pro val   (SEQ ID NO:13)
asn pro ser thr ala pro ala pro thr pro thr pro thr phe
ala gly thr 1.11
gly ala gly val asn val pro ala gly ala gly ala ala ile   (SEQ ID NO:14)
leu thr pro thr pro val asn pro ser thr ala pro ala pro
ala pro NH$_2$ 1.12
gly ala gly ala ala ile leu thr pro thr pro val asn pro   (SEQ ID NO:15)
ser thr ala pro ala pro ala pro thr pro thr phe ala gly
thr gln thr pro 1.13
ala tyr lys phe gly gln pro thr leu thr phe gly ala gly   (SEQ ID NO:16)
val asn val pro ala gly ala gly ala ala ile leu thr pro
thr pro val asn pro ser thr ala pro ala pro ala pro 1.14
ala tyr lys phe glu gln pro thr leu thr phe gly ala gly   (SEQ ID NO:17)
val asn val pro ala gly ala gly ala ala ile leu thr pro
thr pro val asn pro ser thr ala pro ala pro ala pro thr
pro thr phe ala gly thr gln thr pro 1.15
ala tyr lys phe glu gln pro thr leu thr phe gly ala gly   (SEQ ID NO:18)
val asn val pro ala gly ala gly ala ala ile leu thr pro
thr pro val asn pro ser thr ala pro ala pro ala pro NH$_2$ 1.16
gly ala gly val asn val pro ala gly ala gly ala ala ile   (SEQ ID NO:19)
leu thr pro thr pro val asn pro ser thr ala pro ala pro
ala for peptide 2:

2.1
asp met asn pro ala asn trp pro arg glu arg ala trp ala   (SEQ ID NO:20)
leu lys asn pro his leu ala tyr asn pro phe 2.2
asp met asn pro ala asn trp pro arg glu arg ala trp ala   (SEQ ID NO:21)
leu lys asn pro his leu -continued 2.3
pro ala asn trp pro arg glu arg ala trp ala leu lys asn    (SEQ ID NO:22)
pro his leu 2.4
pro ala asn trp pro arg glu arg ala trp ala leu lys asn    (SEQ ID NO:23)
pro his leu ala tyr asn 2.5
trp pro arg glu arg ala trp ala leu lys asn pro his leu    (SEQ ID NO:24)
ala tyr asn pro phe arg 2.6
glu arg ala trp ala leu lys asn pro his leu ala tyr asn    (SEQ ID NO:25)
pro phe arg met pro thr thr 2.7
asp met asn pro ala asn trp pro arg glu arg ala trp ala    (SEQ ID NO:26)
leu 2.8
ala asn trp pro arg glu arg ala trp ala leu lys asn pro    (SEQ ID NO:27)
his leu ala 2.9
asp met asn pro ala asn trp pro arg glu arg ala trp ala    (SEQ ID NO:28)
leu lys asn pro his leu ala tyr asn pro phe arg met pro
thr thr ser thr ala 2.10
arg ala trp ala leu lys asn pro his leu ala tyr asn pro    (SEQ ID NO:29)
phe for peptide 3:

3.1
pro arg ala ala val thr gln thr ala ser arg asp ala ala    (SEQ ID NO:30)

ala ser arg asp ala ala asp glu val trp ala leu arg asp    (SEQ ID NO:31)
gln thr ala Of these, the following peptides are particularly
preferred:

for peptide 1:

1.3(SEQ ID NO:6), 1.4(SEQ ID NO:7), 1.6(SEQ ID NO:9),
1.11(SEQ ID NO:14), 1.13(SEQ ID NO:16)

for peptide 2:

2.1(SEQ ID NO:20), 2.5(SEQ ID NO:24), 2.9(SEQ ID NO:28)
and/or 2.10(SEQ ID NO:29)

for peptide 3:

3.2 (SEQ ID NO:31)

The expressions peptides and polypeptides are used for the purpose of the invention as equivalent to peptides and proteins with up to about 80 AA.

By immunoreactive peptides are generally meant peptides with at least one epitope, where the minimum length of the peptides is generally approximately 6, preferably approximately 8–10 amino acids.

It is often advantageous to derivatize peptides in a variety of ways, such as, for example, by amino-terminal or carboxy-terminal attachment of one or more amino acids, preferably cysteine, in order, for example, to achieve linkage of peptides with one another or to a support. The extensions generally comprise 1 to 40, preferably 1 to 20, in particular 1 to 10 amino acids. Other examples are thioglycolic acid amidation, carboxy-terminal amidation such as, for example, with ammonia or methylamine. Modifications of these types may alter the net charge on the polypeptide and improve the physico-chemical properties of the peptide or facilitate covalent bonding of the peptide to a solid support, to carrier protein or to another peptide.

It is furthermore also possible by replacing individual amino acids by structurally related amino acids to generate immunoreactive mutants. Thus, for example, the amino acid al can be replaced by leu, ile or amino acids which do not occur naturally, such as nva.

In general, modifications of this type do not result in direction alterations in the immunoreactivity of a peptide, although it is perfectly possible to achieve improved immunological properties of the peptides. Thus, for example, methionine is prone to spontaneous oxidation, which can be prevented by replacement by norleucine, without essentially changing the antigenic properties of the polypeptide.

Other amino-acid replacements can take place, for example, within the following groups: gly, ala; val, ile, leu;

asp, glu; asn, gln; ser, thr; lys, arg; phe, tyr; ala, ser; ala, thr; ala, val; ala, pro; ala, glu; leu, gln; gly, phe; ile, ser and ile, met.

The invention therefore also relates to peptides with an amino-acid sequence according to the invention modified by replacement, addition or deletion of one or more amino acids.

It may likewise be advantageous to improve the polypeptide's properties of adsorption onto a support by the addition of a hydrophobic sequence comprising about 2 to 20 hydrophobic amino acids such as, for example, phe ala phe ala phe (SEQ ID NO:32).

It has also been found that mixtures of the peptides according to the invention may have better diagnostic properties than single peptides for an immunochemical anti-HCMV detection.

The invention therefore also relates to mixtures of the peptides according to the invention.

Mixtures of peptides 1, 2 and 3 are particularly suitable, and in turn the following mixtures are particularly preferred: 1.6, (SEQ ID NO:9) 2.1, (SEQ ID NO:20) 3.2; (SEQ ID NO:31) 1.11, (SEQ ID NO:14) 2.1, (SEQ ID NO:20) 3.2; (SEQ ID NO:31) 1.6, (SEQ ID NO:9) 2.10, (SEQ ID NO:29) 3.2; (SEQ ID NO:31) 1.11, (SEQ ID NO:14) 2.10, (SEQ ID NO:29) 3.2; (SEQ ID NO:31) 1.6, (SEQ ID NO:9) 2.7, (SEQ ID NO:26) 3.2 (SEQ ID NO:31) or 1.11, (SEQ ID NO:14) 2.7, (SEQ ID NO:26) 3.2. (SEQ ID NO:31)

However, if a mixture is prepared from the peptides and used to coat, for example, a microtiter plate, there is a risk of unequal coating since the peptides vary in their efficiency of binding to the surface owing to different physical properties.

In another embodiment, therefore, 2 or more of the said peptides, preferably 2 to 10, in particular 2 to 4, peptides are linked with or without spacer. This results in uniform coating of the microtiter plates. It is even possible to prepare polymeric forms of two or more peptides by methods known to the person skilled in the art, so that multiple immunorelevant epitopes are present on one peptide. The peptides according to the invention can, as already mentioned, also be bound to a carrier such as, for example, protein or latex particle. Thus, particularly suitable as carrier or else as bridge are, for example, human serum albumin and/or polylysine.

Modifications of these types generally alter the passive adsorption or property of covalent bonding to the solid phase in a beneficial way, have an advantageous effect on the coupling method or act more strongly as antigen in the generation of polyclonal or monoclonal antibodies directed against the peptides.

The invention therefore also relates to peptides which are linked together with or without bridge, or can also be bound to a carrier.

The said immunoreactive peptides can be prepared by synthesis or genetic manipulation, preferably by synthesis by methods known to the person skilled in the art.

They can be synthesized both in the form of one peptide and in the form of a mixture of a plurality of small peptides with overlapping or non-overlapping amino-acid sequence.

The polypeptides prepared by genetic manipulation also include fusion proteins whose fusion portion has subsequently been eliminated. They also include polypeptides which can be modified where appropriate, for example, by glycosylation, acetylation or phosphorylation. Solid-phase synthesis, especially the Fmoc method of G. B. Fields and R. L. Noble has preferably been used for the chemical peptide synthesis. Using this method the peptides according to the invention can be prepared, for example, in a semiautomatic or completely automatic peptide synthesizer on polystyrene (1% divinylbenzene) using anchors suitable for Fmoc. A carboxyl or carboxamide functionality, for example, can be used at the C terminus. In the case of a carboxyl group it is possible and preferable to use alkoxybenzyl alcohol as anchor on the resin. Peptide amides can be synthesized, for example, on[(5-carboxylatoethyl-2,4-dimethoxyphenyl)-4'-methoxyphenyl]methylamine resin by the method of Breipohl et al. (G. Breipohl, J. Knolle and W. Stüber, Int. J. Peptide, Protein Res. 34, 1989, 252–267). The initial loadings of the resins were generally in the range 0.2–1.0 mmol, preferably 0.4–0.6 mmol of amino functionalities/gram. The syntheses were carried out by the following general reaction sequence:

1. Resin washed, for example with DMF.
2. Resin treated with a solvent mixture such as, for example, piperidine/DMF.
3. Resin washed, preferably first with DMF/isopropanol and then with DMF.
4. Resin reacted with a 1–6-fold, preferably 2–4-fold, in particular 2.5–3.5-fold, excess of activated amino-acid derivative, for example of a Fmoc-activated amino acid. The amino-acid derivative was activated, for example, with DIC/HOBt or TBTU/DIPEA in DMF.
5. Reaction steps 3 and 4 repeated.

After the required peptide had been synthesized the peptides were cleaved off the resin, for example by treatment with 90% TFA, 5% ethanedithiol, 5% resorcinol at room temperature. The peptide which has been cleaved off can subsequently be crystallized from ether and purified by general methods such as HPLC, ion exchange chromatography or gel permeation. The composition of the peptides can be checked by amino-acid analysis and/or mass spectrometry, and the purity can be tested, for example, by HPLC.

Bridged peptides were likewise prepared by generally known methods. The following possibilities, inter alia, exist for the bridging:

A) direct amide linkage;
B) bridging via a peptide with 1 to 10, preferably 1 to 5, in particular 1–3, amino acids;
C) thioether or disulfide bridge.

The peptides bridged with an amino acid or a short peptide can be synthesized by the abovementioned method. An example of a suitable short peptide is a triglycine. Joining the two peptides via a so-called spacer, in particular via a hydrophobic spacer, generally has, as already mentioned, a beneficial effect on the interaction of the microtiter plate. A particularly preferred amino acid as bridging element is, for example, epsilon-amino-caproic acid.

Thioether or disulfide bridges are obtained by synthesizing a maleimide functionality at the N terminus of one peptide and introducing a sulfhydryl group, preferably in the form of cysteine, at the C or N terminus of the other peptide, and subsequently linking the two peptides. This linkage can take place both on a solid support and in solution.

An immunochemical detection generally comprises methods which permit the determination of antigens and/or antibodies in body fluids such as serum, plasma, saliva, cerebrospinal fluid or urine as homogeneous (in solution) or heterogeneous (with solid phase) methods. These are also called immunoassays, and examples are enzyme immunoassay (ELISA or EIA), radioimmunoassay (RIA), immunofluorescence assay (IFA), radioimmunoprecipitation assay (RIPA) or agar gel diffusion assay etc.

These numerous, very different methods differ in specific embodiments, in the marker used for detection or measuring principle (for example photometrically, radiometrically, visually or by aggregation, scattered light or precipitation behavior) and in the solid phases. The person skilled in the art is aware that separation of bound and free sample antibodies or antigen is, although widely used, not absolutely necessary such as, for example, in so-called homogeneous assays. Heterogeneous immunoassays are preferred, especially heterogeneous ELISA methods.

The antibody detection in an immunochemical detection method entails contacting the sample with the described peptide sequences during the procedure, in order to form an antigen-antibody complex in a particular step of the relevant method, or to prevent the formation thereof in competitive and inhibition assays by adding suitable labeled reagents.

The invention therefore also relates to an immunochemical method for the detection and/or for the determination of HCMV antibodies using the peptides according to the invention and to an assay kit therefor.

In the direct methods, the antibodies can be contacted with peptides bound to a solid phase or with labeled peptides or with both, it being irrelevant whether the fundamental method is based as 1-, 2- or multistep method on the principle of the second antibody assay or on the immunometric assay design (double-antigen sandwich) either with identical or different peptides (or peptide mixtures) on the solid phase and as liquid reagent for the detection and in conjunction with specific so-called capture antibodies (for example anti-IgM) or affinity reagents (for example protein A).

The peptides can be linked to the solid phase covalently, by adsorption or by means of specific antibodies or similar affinity methods, for example via the biotin/avidin complex, but adsorption is preferred.

Suitable as support material for the solid phase are plastics such as polystyrene, polyvinyl chloride, polyamide and other synthetic polymers, natural polymers such as cellulose and derivatized natural polymers such as cellulose acetate and nitrocellulose, as well as glass, especially as glass fibers. Polystyrene is preferred as support material.

The supports can be in the form of beads, rods, tubes and microtiter plates or in the form of suspensions such as, for example, latex particles. Sheet-like structures such as paper strips, disks and membranes are likewise suitable. The surface of the supports can be both permeable and impermeable to aqueous solutions.

Preferred supports are beads, tubes, wells, microparticles, paper strips and membranes. Particularly preferred supports are microtiter plates, latex particles, polystyrene beads or magnetically attractable particles.

The peptide concentration for coating the support is generally about 0.01–20 $\mu$g/ml, preferably 0.01–10 $\mu$g/ml, particularly preferably 2–10 $\mu$g/ml.

It is particularly advantageous to use synthetically prepared polypeptides whose high purity and strong antigenicity allows very small amounts to be used, for example 0.01–2.0 $\mu$g/ml, preferably 0.1–0.5 $\mu$g/ml. The binding capacity of the support, in particular when polystyrene is used, is generally not saturated so that it is normally possible to coat with a plurality of different polypeptides, in particular with 2–5, especially with 3–4, different polypeptides, which is a particular advantage.

When the peptides are used as labeled derivatives for the detection, all coupling techniques known to the person skilled in the art are suitable. It is also possible to apply multistage methods such as, for example, preformed peptide-antibody complexes in which the antibody carries the labeling, or high-affinity systems such as, for example, biotin/avidin with labeling of one of these reactants.

Examples of markers which can be used are radioactive isotopes, fluorescent or chemiluminescent dyes. Markers which can also be used are enzymes which, for example, are detected by chromogenic, luminogenic or fluorogenic substrate systems or by subsequent amplifier systems with a second enzyme which is activated by the first.

The markers preferably used are enzymes, especially the alkaline phosphatase and/or horseradish peroxidase or chemiluminogenic compounds such as, for example, acridinium esters.

The labeling is carried out by methods which are described in the prior art for the said markers. In the case of labeling of the antibodies with peroxidase it is possible to use the periodate technique of NAKANE et al., 1974, J. Histochem. Cytochem. 22, 1084–1090, or a method of ISHIKAWA et al., 1983, J. Immunoassay 4, 209–327, in which the partners are linked by a heterobifunctional reagent.

Besides these methods it is possible to use the peptides for sensitizing suitable surfaces such as, for example, latex or erythrocytes in order to measure automatically or visually the physicochemical changes induced by peptide-specific antibodies, such as, for example, precipitations, aggregation or light scattering. It is known that it is also possible to employ the peptides underivatized for the inhibition of these measurement principles as well as the abovementioned methods.

The antigens can be detected using immunodiagnostic methods which make use of polyclonal or monoclonal antibodies which are prepared using the peptides according to the invention or derivatives thereof. The embodiments suitable for the detection method are known to the person skilled in the art and comprise formation in a particular step of antibody-antigen complexes or inhibition of complex formation in competitive methods by adding a labeled antigen.

The invention therefore also relates to an immunochemical method for the detection and/or determination of HCMV antigen using antibodies against the peptides according to the invention, and the assay kit therefor.

Suitable as solid phases, markers or measurement principle for the establishment of an antigen assay are all the possibilities explained for the corresponding antibody determination, with the competitive principle and the double antibody sandwich technique being particularly preferred as immunochemical method. It is immaterial in this connection whether the methods are designed as 1-, 2- or 3-step methods. Thus, multistep methods can be carried out with unlabeled detection antibodies which are determined with the aid of another antibody which is directed against them and is appropriately labeled. It is advantageous for the generation of the antibodies to modify the peptides in such a way that their immunogenic property is improved as is possible, for example, by coupling to natural proteins, such as, for example, to serum proteins such as gamma globulin or serum albumin, to hemocyanins such as KLH=keyhole limpet hemocyanin or toxoids such as diphtheria or tetanus toxoid (B. S. Schaffhausen in Hybridoma Technologie in the Biosciences and Medicine, ed. T. A. Springer, Plenum Press NY, London 1985).

Finally, the present invention can also be applied when using an immunodiagnostic element which contains the solid phase and, in dry form, a part or else all of the reagents required, and in this case too the new peptides are either present on the solid phase or in the detection reagent or in both, and an antibody determination, an antigen detection or combinations with other analytes is carried out.

The peptides according to the invention can be tested by, for example, coating a microtiter plate with the peptides. The coating is generally carried out in a buffer solution, for example in a carbonate, phosphate or trishydroxymethylaminomethane buffer, preferably in a carbonate buffer. After the coating, the plates were incubated with serum samples in a dilution of 1:1 to 1:250, preferably 1:1 to 1:10, in particular 1:1.5 to 1:2.5. Subsequently the antigen-antibody complex was detected by the methods indicated above, for example using a labeled second antibody against the antigen-antibody complex (immunoassay).

The invention also relates to an immunochemical method and a combination kit therefor for the detection and/or for the determination of a plurality of different antibody specificities each against different pathogens, wherein one or more of the HCMV peptides according to the invention and one or more immunoreactive peptides from other pathogens are immobilized on a support, and the antibodies against them are detected by the abovementioned methods, differentially or non-differentially, preferably differentially.

It is possible to employ in the combination assay virus species related to HCMV, such as, for example, the herpes viruses herpes simplex 1 and/or 2 (HSV 1/2), Epstein-Barr virus (EBV), varicella zoster virus (VZV) or human herpes virus 6 (REV 6) and/or unrelated virus species such as, for example, the hepatitis viruses HAV, HBV, HCV or else the viruses HIV1 and HIV2. In particular, it is possible to employ mixtures of HCMV peptides and one or more peptides and/or recombinant proteins of other pathogens in the combination assay, in which case the peptides ought not to have any measurable cross-reactivity with one another.

The peptides according to the invention, the immunoreactive parts and mutants thereof are suitable, for example, for HCMV diagnosis and vaccination. The peptides can also be used as coating antigens for various diagnostic assay systems which operate with various surfaces, for example enzyme immunoassay, magnetic and latex particles, test strips, films and papers manufactured in various ways etc.

One advantage of the immunoreactive peptides according to the invention is a high sensitivity and specificity for the detection of HCMV antibodies so that, besides diluted, it is also possible to use undiluted or only slightly diluted samples. Another advantage of the peptides is that, because of their relatively short sequence length, they can be chemically synthesized simply and in high yield. Chemical synthesis has the advantage that the synthetic peptides are free of cell-specific proteins.

The invention furthermore relates to DNA sequences which code for at least one of the peptides according to the invention.

The invention also relates to an analytical method for the detection and/or for the determination of ECMV, wherein a hybridization reaction which uses at least one nucleic acid probe which in its specific part is complementary to at least one of the DNA sequences according to the invention is employed as specific step.

The invention also relates to polyclonal and/or monoclonal antibodies which are directed against one or more of the peptides according to the invention. The antibodies can be obtained by immunization of a suitable donor, for example a rabbit, with the peptides according to the invention by generally known methods.

The invention also relates to vaccines against HCMV which contain at least one of the peptides according to the invention or antibodies against them.

The invention also relates to an immunoassay which contains at least one of the peptides according to the invention, in particular a heterogeneous immunoassay.

| List of abbreviations | |
|---|---|
| DIC | Diisopropylcarbodiimide |
| DIPEA | Diisopropylethylamine |
| DMF | Dimethylformamide |
| Bop | 1-Benzotriazolyloxytris(dimethylamino)phosphonium hexafluorophosphate |
| Fmoc | Fluorenylmethoxycarbonyl |
| HOBt | Hydroxybenzotriazole |
| TBTU | 2-(1H-Benzotriazol-1-yl)-1,1,3,3-tetramethyl-uronium tetrafluoroborate |

The following examples are intended to explain the invention in detail without, however, restricting it thereto:

EXAMPLES

1. Preparation of Gly Ala Gly Val Asn Val Pro Ala Gly Ala Gly Ala Ala Ile Leu Thr Pro Thr Pro Val Asn Pro Ser Thr Ala Pro Ala Pro Ala Pro-amide (peptide 1.11) (SEQ ID NO:14)

1.06 g of Fmoc-amide anchor resin were reacted in a completely automatic peptide synthesizer (Advanced ChemTech$^R$, Louisville, Ky., USA) in accordance with the manufacturer's instructions. The amino-acid excess was 3-fold. The reaction time per amino-acid derivative was 30 minutes. 506 mg of Fmoc-proline was employed, together with 213 mg of HOBt and 697 mg of Bop (in place of TBTU), as first amino acid. 3 Mmol of diisopropylethylamine were added as base. The carboxamide functionality was derivatized with trityl. The synthesis was carried out by the following reaction sequence (for 1 g of resin):

| 1 | Resin washed 3 times with 15 ml of DMF each time |
|---|---|
| 2 | Resin treated with 15 ml of 20% piperidine/DMF (3 min) |
| 3 | Resin treated with 15 ml of 20% piperidine/DMF (10 min) |
| 4 | Resin washed 3 times alternately with DMF/iso-propanol |
| 5 | Resin washed twice with DMF |
| 6 | Amino-acid derivative introduced in 3-fold excess and activated either with DIC/HOBt or with TBTU/DIPEA in DMF and shaken with the resin for 30 min |
| 7 | Resin washed twice alternately with DMF/iso-propanol |

At the end of the coupling reactions, the peptide resin was washed with methanol and diethyl ether and dried under high vacuum. 2.36 grams of peptide resin were stirred with 27 ml of trifluoroacetic acid/1.5 gram of resorcinol/1.5 ml of ethanedithiol at room temperature for 1.5 hours and crystallized in diethyl ether. The crude peptide was washed with diethyl ether and dried under high vacuum (yield 1090 mg). The peptide was chromatographed on Sephadex G-25 in 0.5% acetic acid, and the peptide fraction was isolated by freeze drying (yield 654 mg). The purity of the substance was tested by HPLC. The correct composition was confirmed by amino-acid analysis. The peptide content was 86%.

2. Testing of the Peptides

A microtiter plate with 96 wells was coated with a synthesized peptide. To do this, a solution of 2.5 µg of peptide per ml of carbonate buffer was made up and introduced in 100 µl portions into the wells for the coating. The peptides were adsorbed onto the surfaces at 4° C. overnight and, after removal of the peptide solution, the wells were washed several times with washing buffer (50 mM Tris, pH 7.2, 10 mM EDTA, 0.2% Tween 20). Then individual human serum samples in a 1:2 dilution were introduced and incubated at 37° C. for 1 hour. After another washing step, the conjugate antibody specific for human IgG antibodies or human IgM antibodies and labeled with peroxidase was added and the mixture was incubated at room temperature for 0.5 hour. The reaction was subsequently stopped by adding 0.5 M sulfuric acid and extinction of the individual samples was measured at a wavelength of 450/650 nm in a photometer.

3. Localization of Relevant Epitopes

To test the immunogenicity, peptides of various length from the complete amino-acid sequence region from 718 to 880 of the HCMV protein pp150 (Tab. 2 and 3) were synthesized as described in Example 1. Subsequently, as in Example 2, the microtiter plates were coated with the synthesized peptides, and the immunological reactivity was assayed. The result of the series of assays was that all the tested HCMV-positive sera reacted in particular with at least one of the three specific sequence regions, whereas the other sequence regions showed only a weak immunological reaction (Tab. 2 and 3). The three immunologically reactive peptides have the following sequences:

| | |
|---|---|
| $AS_e$-gly ala gly ala ala ile leu-$BS_m$ | (peptide 1)(SEQ ID NO: 1) |
| $CS_n$-arg ala trp ala leu -$DS_o$ and/or | (peptide 2)(SEQ ID NO: 2) |
| $ES_p$-ala ser arg asp ala ala-$FS_q$ | (peptide 3)(SEQ ID NO: 3) |
| where AS, BS, CS, DS, ES and FS are, independently of one another, any appropriate amino acid and | |
| e | are, independently of one another, integers from 0 to 22, |
| m | are, independently of one another, from 0 to 25, |
| n and o | are, independently of one another, from 0 to 18 |
| and | |
| p and q | are, independently of one another, from 0 to 11. |

It was possible in this way to differentiate sera which reacted either with all or else only with one or two sequence regions.

Demonstrably HCMV-negative sera did not react with the three peptides.

4. Diagnostic Use of the Peptides According to the Invention

In order to test the immunoreactivity of the peptides found, a mixture of peptides 1.11, (SEQ ID NO:14) 2.10 (SEQ ID NO:29) and 3.2 (SEQ ID NO:31)—total concentration 2.5 µg/ml with a mixing ratio of 1:1:1 (by weight)—were introduced as an antigen into microtiter plates as in Example 2, and the assay was carried out as described therein. Used in this case was a defined and previously tested group of sera which had already been assayed in a conventional assay for IgM and IgG reactivity; reference assays: CMV Enzygnost$^R$ IgM-POD and CMV Enzygnost$^R$ IgG-POD, Behringwerke AG, Marburg. The indicated assay configuration is very suitable for diagnosing the HCMV immune status both for IgM and for IgG antibody detection (Tab. 4 and 5).

5. Reaction of the monoclonal antibody 87–55/02 with one of the identified peptide epitopes A monoclonal antibody which has an unambiguous immunological reaction with the HCMV protein pp150 and one with the recombinant protein section pXP1, measured as immunoblot and ELISA reactivity, was investigated on an ELISA microtiter plate which had been coated with various synthesized peptides in Table 3 at the same concentration (0.25 µg/well). After development of the plate with said antibody, the reaction with the peptide 2.7, which had previously been identified as an important epitope, was very clearly distinct. It was concluded from the method for selecting the monoclonal antibody that the identified epitope must have a very important structure which is not even destroyed by denaturation of the complete protein. This monoclonal antibody correspondingly reacts both with the synthesized peptide 2.7 (SEQ ID NO:26) and with the recombinant protein XP1 (SEQ ID NO:33) and the pp150 protein of HCMV.

TABLE 1

(SEQ ID NO: 33)
Amino-acid sequence of XP1 (amino acid 718–880 of HCMV protein pp150)

| 1 | DPRFTDTLVD | ITDTETSAKP | PVTTAYKFEQ | PTLTFGAGVN | VPAGAGAAIL |
|---|---|---|---|---|---|
| 51 | TPTPVNPSTA | PAPAPTPTFA | GTQTPVNGNS | PWAPTAPLPG | DMNPANWPRE |
| 101 | RAWALKNPHL | AYNPFRMPTT | STASQNTVST | TPRRPSTPRA | AVTQTASRDA |
| 151 | ADEVWALRDQ | TA | | | |

TABLE 2

Individual reactivities of the synthetic peptides from the XP1 region of the HCMV protein pp150

The individual reactivities of the synthetic pXP1 segments with the assayed group of CMV IgG-positive sera are reported in percent.

1. asp pro arg phe thr asp thr leu val asp ile thr asp thr glu thr ser ala lys pro pro val (SEQ ID NO: 34)
   Reactivity    20%
2. ala pro ala pro ala pro thr pro thr phe ala gly thr gln thr pro val asn gly asn ser (SEQ ID NO: 35)
   Reactivity    20%
3. ala pro thr ala pro leu pro glyasp met asn pro ala (SEQ ID NO: 36)
   Reactivity    30%
4. gln asn thr val ser thr thr pro arg argpro ser thr pro arg ala ala val thr gln thr ala (SEQ ID NO: 37)
   Reactivity    40%
5. asp met asn pro ala asn trp pro arg glu arg ala trp ala leu
   Reactivity    60%        (Peptide 2.7)(SEQ ID NO: 26)
6. arg ala trp ala leu lys asn pro his leu ala tyr asn pro phe
   Reactivity    80%        (Peptide 2.10)(SEQ ID NO: 29)
7. gly thr gln thr pro val asn gly asn ser pro trp ala pro thr ala (SEQ ID NO: 38)
   Reactivity    20%
8. pro val thr thr ala tyr lys phe glu gln pro thr leu thr phe (SEQ ID NO: 39)
   Reactivity    10%
9. leu thr phe gly ala gly val asn val pro ala gly ala gly ala ala ile leu (SEQ ID NO: 40)
   Reactivity    60%
10. ile leu thr pro thr pro val asn pro ser thr ala pro ala (SEQ ID NO: 41)
    Reactivity    40%
11. pro phe arg met pro thr thr ser thr ala ser gln asn thr val (SEQ ID NO: 42)
    Reactivity    60%
12. ala ser arg asp ala ala asp glu val trp ala leu arg asp gln thr ala
    Reactivity    80%        (Peptide 3.2)(SEQ ID NO: 31)
13. gly ala gly val asn val pro ala gly ala gly ala ala ile leu thr pro thr pro val asn pro ser thr ala pro ala pro ala pro NH2
    Reactivity    90%        (Peptide 1.11)(SEQ ID NO: 14)

TABLE 2-continued

Individual reactivities of the synthetic peptides from the XP1 region of the HCMV protein pp150

14. glu thr ser ala lys pro pro val thr thr ala tyr lys phe glu (SEQ ID NO: 43)
    Reactivity    10%
15. lys phe glu gln pro thr leu thr phe gly ala gly val (SEQ ID NO: 44)
    Reactivity    20%
16. ala gly ala ala ile leu thr pro thr pro val (SEQ ID NO: 45)
    Reactivity    40%
17. val asn pro ser thr ala prb ala pro ala pro thr (SEQ ID NO: 46)
    Reactivity    10%
18. his leu ala tyr asn pro phe arg met pro thr thr ser thr ala (SEQ ID NO: 47)
    Reactivity    60%
19. pro arg ala ala val thr gln thr ala ser arg asp ala ala
    Reactivity    60%        (Peptide 3.1)(SEQ ID NO: 30)
20. asp pro arg phe thr asp thr leu val asp ile (SEQ ID NO: 48)
    Reactivity    10%
21. ile thr asp thr glu thr ser ala lys pro pro val thr thr ala tyr lys phe glu gln pro thr leu (SEQ ID NO: 49)
    Reactivity    20%
22. ala asn trp pro arg glu arg ala trp ala leu lys asn pro his leu ala
    Reactivity    70%        (Peptide 2.8)(SEQ ID NO: 27)
23. asp met asn pro ala asn trp pro arg glu arg ala trp ala leu lys asn pro his leu ala tyr asn pro phe
    Reactivity    80%        (Peptide 2.1)(SEQ ID NO: 20)
24. pro thr leu thr phe gly ala gly val asn val pro ala gly ala gly ala ala ile leu thr pro thr pro val asn pro ser thr ala pro ala pro ala pro NH₂
    Reactivity    90%        (Peptide 1.6)(SEQ ID NO: 9)
25. ala tyr lys phe glu gln pro thr leu thr phe gly ala gly val asn val pro ala gly ala gly ala ala ile leu thr pro thr pro val asn pro ser thr ala pro ala pro ala pro NH₂
    Reactivity    85%        (Peptide1.15)(SEQ ID NO: 18)

TABLE 3

Individual reactivities of particularly reactive peptides from the XP1 region of the HCMV protein pp150

The individual reactivities of the synthetic pXP1 segments with the assayed group of CMV IgG-positive sera are reported in percent.
Peptide No. 1

1.1
ala tyr lys phe glu gln pro thr leu thr phe gly ala gly  (SEQ ID NO:4)
val asn val pro ala gly ala gly ala ala ile leu
Reactivity 80%

1.2
phe glu gln pro thr leu thr phe gly ala gly val asn val  (SEQ ID NO:5)
pro ala gly ala gly ala ala ile leu thr pro thr pro val
Reactivity 80%

1.3
phe glu gln pro thr leu thr phe gly ala gly val asn val  (SEQ ID NO:6)
pro ala gly ala gly ala ala ile leu thr pro thr pro val
asn pro ser thr ala
Reactivity 85%

TABLE 3-continued

Individual reactivities of particularly
reactive peptides from the XP1 region of the
HCMV protein pp150

1.4
phe glu gln pro thr leu thr phe gly ala gly val asn val  (SEQ ID NO:7)
pro ala gly ala gly ala ala ile leu thr pro thr pro val
asn pro ser thr ala pro ala pro ala
Reactivity 90%

1.5
pro thr leu thr phe gly ala gly val asn val pro ala gly  (SEQ ID NO:8)
ala gly ala ala ile leu thr pro thr pro val asn pro ser
thr ala pro ala pro ala
Reactivity 80%

1.6
pro thr leu thr phe gly ala gly val asn val pro ala      (SEQ ID NO:9)
gly ala gly ala ala ile leu thr pro thr pro val asn pro
ser thr ala pro ala pro ala pro $NH_2$
Reactivity 90%

1.7
val asn val pro ala gly ala gly ala ala ile leu thr pro  (SEQ ID NO:10)
thr pro val asn pro
Reactivity 70%

1.8
pro ala gly ala gly ala ala ile leu thr pro thr pro val  (SEQ ID NO:11)
asn pro ser thr ala pro ala
Reactivity 70%

1.9
val asn val pro ala gly ala gly ala ala ile leu thr pro  (SEQ ID NO:12)
thr pro val asn pro ser thr ala pro ala pro ala pro thr
pro thr phe
Reactivity 70%

1.10
pro ala gly ala gly ala ala ile leu thr pro thr pro val  (SEQ ID NO:13)
asn pro ser thr ala pro ala pro ala pro thr pro thr phe
ala gly thr
Reactivity 80%

1.11
gly ala gly val asn val pro ala gly ala gly ala ala ile  (SEQ ID NO:14)
leu thr pro thr pro val asn pro ser thr ala pro ala pro
ala pro NH2
Reactivity 90%

1.12
gly ala gly ala ala ile leu thr pro thr pro val asn pro  (SEQ ID NO:15)
ser thr ala pro ala pro ala pro thr pro thr phe ala gly
thr gln thr pro
Reactivity 80%

1.13
ala tyr lys phe glu gln pro thr leu thr phe gly ala gly  (SEQ ID NO:16)
val asn val pro ala gly ala gly ala ala ile leu thr pro
thr pro val asn pro ser thr ala pro ala pro ala pro
Reactivity 90%

1.14
ala tyr lys phe glu gln pro thr leu thr phe gly ala gly  (SEQ ID NO:17)
val asn val pro ala gly ala gly ala ala ile leu thr pro
thr pro val asn pro ser thr ala pro ala pro ala pro thr
pro thr phe ala gly thr gln thr pro
Reactivity 60%

1.15
ala tyr lys phe glu gln pro thr leu thr phe gly ala gly  (SEQ ID NO:18)
val asn val pro ala gly ala gly ala ala ile leu thr pro
thr pro val asn pro ser thr ala pro ala pro ala pro $NH_2$
Reactivity 85%

TABLE 3-continued

Individual reactivities of particularly
reactive peptides from the XP1 region of the
HCMV protein pp150

1.16
gly ala gly val asn val pro ala gly ala gly ala ala ile  (SEQ ID NO:19)
leu thr pro thr pro val asn pro ser thr ala pro ala pro
ala
Reactivity 70%

Peptide No. 2

2.1
asp met asn pro ala asn trp pro arg glu arg ala trp ala  (SEQ ID NO:20)
leu lys asn pro his leu ala tyr asn pro phe
Reactivity 80%

2.2
asp met asn pro ala asn trp pro arg glu arg ala trp      (SEQ ID NO:21)
ala leu lys asn pro his leu
Reactivity 75%

2.3
pro ala asn trp pro arg glu arg ala trp ala leu lys      (SEQ ID NO:22)
asn pro his leu
Reactivity 70%

2.4
pro ala asn trp pro arg glu arg ala trp ala leu lys      (SEQ ID NO:23)
asn pro his leu ala tyr asn
Reactivity 70%

2.5
trp pro arg glu arg ala trp ala leu lys asn pro his      (SEQ ID NO:24)
leu ala tyr asn pro phe arg
Reactivity 80%

2.6
glu arg ala trp ala leu lys asn pro his leu ala tyr      (SEQ ID NO:25)
asn pro phe arg met pro thr thr
Reactivity 70%

2.7
asp met asn pro ala asn trp pro arg glu arg ala trp      (SEQ ID NO:26)
ala leu
Reactivity 60%

2.8
ala asn trp pro arg glu arg ala trp ala leu lys asn pro  (SEQ ID NO:27)
his leu ala
Reactivity 70%

2.9
asp met asn pro ala asn trp pro arg glu arg ala trp ala  (SEQ ID NO:28)
leu lys asn pro his leu ala tyr asn pro phe arg met pro
thr thr ser thr ala
Reactivity 80%

2.10
arg ala trp ala leu lys asn pro his leu ala tyr asn pro  (SEQ ID NO:29)
phe
Reactivity 80%

Peptide No. 3

3.1
pro arg ala ala val thr gln thr ala ser arg asp ala ala  (SEQ ID NO:30)
Reactivity 60%

3.2
ala ser arg asp ala ala asp glu val trp ala leu arg asp  (SEQ ID NO:31)
gln thr ala
Reactivity 80%

TABLE 4

IgM reactivity of the peptide mixture

| Assessment | Reference assay | Peptide assay |
| --- | --- | --- |
| positive | 22 | 21 |
| negative | 13 | 13 |
| false-positive | 0 | 0 |
| false-negative | 0 | 1 |
| Number of IgM sera assayed: | | 35 |
| Sensitive: | | 95.5% |
| Specificity: | | 100% |

TABLE 5

IgG reactivity of the peptide mixture

| Assessment | Reference assay | Peptide assay |
| --- | --- | --- |
| positive | 133 | 132 |
| negative | 152 | 149 |
| false-positive | 0 | 3 |
| false-negative | 0 | 1 |
| Number of IgG sera assayed: | | 285 |
| Sensitive: | | 95.25% |
| Specificity: | | 98.03% |

What is claimed is:

1. A support-bound peptide which reacts specifically with antibodies against HCMV protein pp 150, consisting of at least one sequence selected from the group consisting of Peptide 1, Peptide 2, and Peptide 3, wherein
Peptide 1 consists of SEQ ID NO:1 (gly ala gly ala ala ile leu) with
0 to 14 additional N-terminal amino acids and 0–7 additional C-terminal amino acids, or
0 to 2 additional N-terminal amino acids and 0 to 19 additional C-terminal amino acids;
Peptide 2 consists of SEQ ID NO:2 (arg ala trp ala leu) with
0 to 18 additional N-terminal amino acids and 0 to 18 additional C-terminal amino acids; and
Peptide 3 consists of SEQ ID NO:3 ( ala ser arg asp ala ala) with
0 to 11 additional N-terminal amino acids and 0 to 11 additional C-terminal amino acids;
wherein said additional amino acids comprise contiguous amino acids of HCMV protein pp150.

2. An immunological assay kit for the determination or detection of HCMV antibodies comprising one or more of the support-bound peptides of claim 1.

3. The assay kit as claimed in claim 2, wherein the support is selected from the group consisting of beads, rods, tubes, films, fibers, test strips, microparticles, paper strips disks, or membranes; and microtiter plates.

4. The assay kit as claimed in claim 2, wherein the support is selected from the group consisting of glass fibers, polystyrene beads, protein, latex particles, and magnetically attractable particles.

5. The assay kit as claimed in claim 2, wherein the support is selected from the group consisting of polyvinyl chloride, polyamide cellulose, cellulose acetate, nitrocellulose, and glass.

6. The assay kit as claimed in claim 2, wherein the support is polystyrene.

7. The assay kit as claimed in claim 2, wherein the support is a sheet-like structure.

8. The assay kit as claimed in claim 2, wherein the support is selected from the group consisting of synthetic polymers, natural polymers, and derivatized natural polymers.

9. The assay kit of claim 2, wherein at least one peptide is a labeled derivative.

10. The assay kit of claim 2, further comprising at least one marker.

11. The assay kit as claimed in claim 10, wherein the at least one marker comprises enzyme-labeled, fluorescence-labeled, chemiluminescence-labeled, biotin-labeled, or radiolabeled antibodies against the peptide-bound antibodies.

12. The assay kit as claimed in claim 11, wherein the enzyme-labeled antibodies are labeled with either alkaline phosphatase, horseradish peroxidase, or both.

13. The assay kit of claim 2, wherein a multiplicity of the HCMV peptides are bound to at least one support.

14. The assay kit of claim 2, wherein antibody binding to a multiplicity of peptide sequences may be simultaneously detected or determined.

15. The assay kit of claim 2, wherein at least one support-bound peptide comprises at least two of the sequences defined in claim 1 linked together directly or via a spacer.

16. The assay kit of claim 15, wherein the at least two peptides comprise at least two different HCMV sequences.

17. The assay kit of claim 15, wherein the spacer is either human serum albumin, or polylysine, or both.

18. The assay kit of claim 15, wherein the spacer is an amide, thioether, or disulfide bridge, or a short peptide which does not comprise additional contiguous amino acids of pp150.

19. The assay kit of claim 15, wherein the spacer is triglycine, epsilon-amino-caproic acid, or cysteine.

20. The assay kit of claim 2, further comprising one or more immunoreactive peptides and/or recombinant proteins from pathogens other than HCMV immobilized on one or more supports.

21. The assay kit of claim 20, wherein said one or more immunoreactive peptides and/or recombinant proteins from pathogens other than HCMV is an immunoreactive peptide or recombinant protein from HSV 1/2, EBV, VZV, HHV6, HAV, HBV, HCV, or HIV 1/2.

22. The assay kit of claim 20, wherein the kit contains components to carry out a differential assay.

23. The assay kit of claim 2, wherein at least one peptide is bound to the support by an N-terminal or C-terminal linker of about 1–40 amino acids, and the linker does not comprise additional amino acids of pp 150 contiguous with the at least one peptide.

24. The assay kit of claim 23, wherein the linker comprises about 2 to 20 hydrophobic amino acids.

25. The immunological assay kit of claim 2, wherein the HCMV antibodies to be determined or detected are HCMV antibodies in body fluids.

26. The immunological assay kit of claim 25, wherein the body fluids are selected from the group consisting of serum, plasma, saliva, cerebrospinal fluid, and urine.

27. An immunochemical method for the detection or for the determination of HCMV antibody comprising:
   1) contacting a sample with at least one support-bound peptide which reacts specifically with antibodies against HCMV protein pp150, consisting of at least one sequence selected from the group consisting of Peptide 1, Peptide 2, and Peptide 3, wherein
       Peptide 1 consists of SEQ ID NO:1 (gly ala gly ala ala ile leu) with
           0 to 14 additional N-terminal amino acids and 0–7 additional C-terminal amino acids, or
           0 to 2 additional N-terminal amino acids and 0 to 19 additional C-terminal amino acids;
       Peptide 2 consists of SEQ ID NO:2 (arg ala trp ala leu) with
           0 to 18 additional N-terminal amino acids and 0 to 18 additional C-terminal amino acids; and
       Peptide 3 consists of SEQ ID NO:3 (ala ser arg asp ala ala) with
           0 to 11 additional N-terminal amino acids and 0 to 11 additional C-terminal amino acids;
       wherein said additional amino acids comprise contiguous amino acids of HCMV protein pp150;
   2) forming a peptide-antibody complex; and
   3) detecting or determining said peptide-antibody complex.

28. The immunochemical method as claimed in claim 27, wherein the support is selected from the group consisting of beads, rods, tubes, films, fibers, test strips, microparticles; paper strips, disks, or membranes; and microtiter plates.

29. The immunochemical method as claimed in claim 27, wherein the support is selected from the group consisting of glass fibers, polystyrene beads, protein, latex particles, and magnetically attractable particles.

30. The immunochemical method as claimed in claim 27, wherein the support is selected from the group consisting of polyvinyl chloride, polyamide cellulose, cellulose acetate, nitrocellulose, and glass.

31. The immunochemical method as claimed in claim 27, wherein the support is a sheet-like structure.

32. The immunochemical method as claimed in claim 27, wherein the support is selected from the group consisting of synthetic polymers, natural polymers, and derivatized natural polymers.

33. The immunochemical method as claimed in claim 27, wherein the support is polystyrene.

34. The immunochemical method of claim 27, wherein at least one peptide is a labeled derivative.

35. The immunochemical method of claim 27, wherein the peptide-antibody complex is detected or determined using at least one marker.

36. The immunochemical method as claimed in claim 35, wherein the at least one marker comprises enzyme-labeled, fluorescence-labeled, chemiluminescence-labeled, biotin-labeled, or radiolabeled antibodies against the peptide-bound antibodies.

37. The immunochemical method as claimed in claim 35, wherein the enzyme-labeled antibodies are labeled with either alkaline phosphatase, horseradish peroxidase, or both.

38. The immunochemical method of claim 27, wherein a multiplicity of the HCMV peptides are bound to at least one support.

39. The immunochemical method of claim 27, wherein antibody binding to a multiplicity of peptide sequences may be simultaneously detected or determined.

40. The immunochemical method of claim 27, wherein at least one support-bound peptide comprises at least two of the sequences defined in claim 27 linked together directly or via a spacer.

41. The immunochemical method of claim 40, wherein the at least two peptides comprise at least two different HCMV sequences.

42. The immunochemical method of claim 41, wherein the spacer is either human serum albumin, or polylysine, or both.

43. The immunochemical method of claim 41, wherein the spacer is an amide, thioether, or disulfide bridge, or a short peptide which does not comprise additional contiguous amino acids of pp150.

44. The immunochemical method of claim 41, wherein the spacer is triglycine, epsilon-amino-caproic acid, or cysteine.

45. The assay kit of claim 27, wherein at least one peptide is bound to the support by an N-terminal or C-terminal linker of about 1–40 amino acids, and the linker does not comprise additional amino acids of pp150 contiguous with the at least one peptide.

46. The assay kit of claim 45, wherein the linker comprises about 2 to 20 hydrophobic amino acids.

47. The immunochemical method of claim 27, wherein the sample to be contacted is a body fluid.

48. The immunological assay kit of claim 47, wherein the body fluids are selected from the group consisting of serum, plasma, saliva, cerebrospinal fluid, and urine.

49. An immunochemical combination method for the detection or for the determination of a plurality of antibody specificities against different pathogens, comprising:
   1) contacting a sample with
       (a) one or more immunoreactive peptides from pathogens other than HCMV, and with
       (b) one or more of the support-bound peptides which react specifically with antibodies against HCMV protein pp150, wherein said support-bound peptides consist of at least one sequence selected from the group consisting of Peptide 1, Peptide 2, and Peptide 3, wherein
           Peptide 1 consists of SEQ ID NO:1 (gly ala gly ala ala ile leu) with
               0 to 14 additional N-terminal amino acids and 0–7 additional C-terminal amino acids, or
               0 to 2 additional N-terminal amino acids and 0 to 19 additional C-terminal amino acids;

Peptide 2 consists of SEQ ID NO:2 (arg ala trp ala leu) with 0 to 18 additional N-terminal amino acids and 0 to 18 additional C-terminal amino acids; and Peptide 3 consists of SEQ ID NO:3 ( ala ser arg asp ala ala) with
0 to 11 additional N-terminal amino acids and 0 to 11 additional C-terminal amino acids;
wherein said additional amino acids comprise contiguous amino acids of HCMV protein pp150.

2) forming at least one type of peptide-antibody complex; and 3) detecting or determining at least one type of peptide-antibody complex.

50. The immunochemical combination method of claim 49, wherein one or more immunoreactive peptides and/or recombinant proteins from pathogens other than HCMV are bound to a support.

51. The immunochemical combination method of claim 49, wherein said one or more immunoreactive peptides and/or recombinant proteins from pathogens other than HCMV is an immunoreactive peptide and/or recombinant protein from HSV 1/2, EBV, VZV, HHV6, HAV, HBV, HCV, or HIV 1/2.

52. The immunochemical combination method as claimed in claim 49, which method is carried out differentially.

53. The immunochemical combination method of claim 49, wherein at least one type of peptide-antibody complex is detected or determined using at least one marker.

54. The immunochemical method as claimed in claim 53, wherein the at least one marker comprises enzyme-labeled, fluorescence-labeled, chemiluminescence-labeled, biotin-labeled, or radiolabeled antibodies against the peptide-bound antibodies.

55. The immunochemical method as claimed in claim 54, wherein the enzyme-labeled antibodies are labeled with either alkaline phosphatase, horseradish peroxidase, or both.

56. The immunochemical method of claim 54, wherein at least two types of peptide-antibody complexes are simultaneously detected.

57. The immunochemical combination method of claim 49, wherein the sample to be contacted is a body fluid.

58. The immunochemical combination method of claim 57, wherein the body fluids are selected from the group consisting of serum, plasma, saliva, cerebrospinal fluid, and urine.

* * * * *